US007339668B2

(12) United States Patent
Ebersole et al.

(10) Patent No.: US 7,339,668 B2
(45) Date of Patent: Mar. 4, 2008

(54) SPECTROMETER FOR ANALYSIS OF MULTIPLE SAMPLES

(75) Inventors: Matthew D. Ebersole, Sun Prairie, WI (US); John R. Iverson, Stoughton, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 127 days.

(21) Appl. No.: 11/253,853

(22) Filed: Oct. 18, 2005

(65) Prior Publication Data

US 2007/0086006 A1     Apr. 19, 2007

(51) Int. Cl.
G01J 3/42      (2006.01)

(52) U.S. Cl. ............... 356/319; 356/326; 356/342; 356/409

(58) Field of Classification Search .......... 356/319, 356/326, 342, 451, 504, 409; 366/326, 409; 422/82.05, 82.09, 82.11; 436/164, 171, 172
See application file for complete search history.

(56) References Cited

U.S. PATENT DOCUMENTS

| | | | |
|---|---|---|---|
| 4,696,570 A * | 9/1987 | Joliot et al. ............... 356/319 |
| 4,915,502 A | 4/1990 | Brierley |
| 4,991,961 A | 2/1991 | Strait |
| 5,132,811 A * | 7/1992 | Iwaki et al. ............... 359/6 |
| 5,151,172 A | 9/1992 | Kukes et al. |
| 5,153,675 A | 10/1992 | Beauchaine |
| 5,239,361 A | 8/1993 | Burch |
| 5,247,343 A | 9/1993 | Burch |
| 5,276,545 A | 1/1994 | Daun et al. |
| 5,436,454 A | 7/1995 | Bornstein et al. |
| 6,661,509 B2 | 12/2003 | Deck et al. |
| 6,667,808 B2 | 12/2003 | Clermont et al. |
| 2005/0206895 A1 * | 9/2005 | Salmelainen ............... 356/318 |

OTHER PUBLICATIONS

Yokogawa Electric Corporation, "InfraSepc NR800 Fourier Transform Near-Infrared Analyzers General Specifications," (2001).
Yokogawa Electric Corporation, "FT-NIR Analyzer InfraSpec NR800," (2001).
Ikezawa et al, "A multi-channel explosion-proof process FT-NIR analyzer with high SNR and high reliability," Journal of Process Analytical Chemistry, vol. 6 (No. 1), p. 27-30, (2001).
Measurementation Inc., "NR800, An FT-NIR Primer," (2001).
XX, "ABB FTPA2000-260 (FTIR/NIR Spectrometers)," ABB Ltd. (Zurich, CH), (2005).

* cited by examiner

*Primary Examiner*—Gregory J. Toatley, Jr.
*Assistant Examiner*—Abdullahi Nur
(74) *Attorney, Agent, or Firm*—DeWitt Ross & Stevens

(57) ABSTRACT

A spectrometer (100) includes a light source (102) providing output light (106) to the bundled input ends (108) of multiple light pipes (110). The light pipes (110) branch into sets (118) between their input ends (108) and output ends (114), with each set (118) illuminating a sample detector (126) (via a sample chamber (122)) for measuring light scattered or emitted by a sample, or a reference detector (128) for obtaining a reference/datum measurement of the supplied light, so that comparison of measurements from the sample detector (126) and the reference detector (128) allows compensation of the sample detector measurements for drift. Efficient and accurate measurement is further assured by arraying the multiple light pipes (110) in each set (118) about the input bundle (116) so that each set receives at least substantially the same amount of light from the light source (102).

26 Claims, 2 Drawing Sheets

SPECTROMETER FOR ANALYSIS OF MULTIPLE SAMPLES

FIELD OF THE INVENTION

This document concerns an invention relating generally to molecular spectrometry, and more specifically to sample processing arrangements in infrared, near infrared, Raman, and other spectrometers.

BACKGROUND OF THE INVENTION

Spectrometry is a well known technique used to identify the characteristics of gas, liquid, and solid samples, wherein light is directed at a sample and the light leaving the sample is then picked up by a photosensitive detector to be analyzed for changes in wavelength. These changes provide information regarding the composition of the sample, its chemical bonds, and other features.

It is often desirable to take measurements from multiple samples simultaneously (or nearly so) to increase analysis speed. This can be done by providing multiple sample chambers, and then providing a moving mirror which directs illumination from the light source to each chamber in turn (with the light then being received by one or more detectors). While this arrangement is beneficial, developers have sought to eliminate the moving mirror owing to the burdens of its maintenance, and the sequential illumination of the sample chambers also limits analysis speed since a user must await the results from the later chambers in the sequence.

In one known spectrometry arrangement which is believed to be exemplified by the FTPA2000 200 spectrometer (ABB Inc., Norwalk, Conn., US), multiple fiberoptic cables receive light from a lamp, and each cable illuminates a separate sample chamber containing a sample to be analyzed. Return fiberoptic cables then each receive the light from each sample and provide it to a detector (with one detector per each sample chamber and return cable) to provide analytical measurements. This arrangement can therefore provide truly simultaneous sample measurements while eliminating the moving mirror. However, an arrangement of this nature can suffer from drift in its components; for example, changes in ambient temperature can change factors such as detector sensitivity, the refractive index of the fiberoptic cables, etc., which can in turn affect measurement accuracy. Additionally, such an arrangement is also susceptible to measurement uncertainties owing to differences between the different "channels" used to obtain measurements from the different chambers. Different channels can experience different degrees of drift, and it is also difficult to obtain the "same light" (i.e., the same light flux/intensity) into each of multiple cables arrayed about the light source. Beamsplitters (e.g., dichroic mirrors, prisms, etc.) can be used to divide the light from a light source into a number of different beams of approximately equal intensity to supply the input cables, but here too drift, imperfections, etc. limit the ability to exactly match light input to the different input cables.

A similar arrangement, which is believed to be exemplified by the InfraSpec NR800 spectrometer (Yokogawa Electric Corporation, Tokyo, JP), has multiple fiberoptic input cables extending from a light source, with each illuminating a separate sample chamber. Each input cable is provided with a beamsplitter whereby its transmitted light is divided into two portions, one illuminating its sample chamber (and subsequently a sample detector) and one illuminating a reference detector. Comparison of the measurements from the sample and reference detectors beneficially allows the sample detector measurements to be at least partially compensated for drift. However, this arrangement still has the disadvantages that the beamsplitter still may not provide the same light to the sample and to the reference detector, and additionally the input cables may not each receive and provide the same light from the light source.

It would therefore be useful to have available additional spectrometer arrangements which allow simultaneous (or nearly so) measurements from multiple samples, while at the same time minimizing (or compensating for) drift within and between the channels used to measure each sample.

SUMMARY OF THE INVENTION

The invention involves spectrometry devices and methods which are intended to at least partially solve the aforementioned problems. To give the reader a basic understanding of some of the advantageous features of the invention, following is a brief summary of preferred exemplary versions of the invention, with reference being made to the accompanying FIGS. 1a and 1b of the drawings (which are described in greater detail below). As this is merely a summary of the preferred versions, it should be understood that more details may be found in the Detailed Description set forth elsewhere in this document. The claims set forth at the end of this document then define the various versions of the invention in which exclusive rights are secured.

Referring to the exemplary version of the invention schematically depicted in FIGS. 1a and 1b, a spectrometer 100 (e.g., a near infrared spectrometer) includes a light source 102 (in this case an incandescent filament 104) which provides output light 106 to the input ends 108 of multiple light pipes 110, with the output light 106 in FIG. 1a first being passed to an interferometer 112. The multiple light pipes 110 are preferably arranged in a manner exemplified by FIG. 1b, wherein the light pipes 110 each of which extends between its input end 108 and an opposing output end 114 have their input ends 108 arrayed into a closely spaced bundle 116 which receives the output light 106 from the light source 102. The bundled light pipes 110 branch into sets 118 between their input ends 108 and output ends 114, with four sets 118A, 118B, 118C, and 118D being depicted in FIG. 1b (and collectively being referred to as sets 118). Preferably, at least some of the sets 118 include multiple light pipes 110, with each set 118 defining an independent optical path whereby no set 118 receives light from any of the other sets 118. At least some of the light pipes 110 within each set 118 preferably have their input ends 108 spaced from each other within the bundle 116 by the input ends 108 of light pipes 110 of other sets 118, as depicted by the exemplary arrangement in FIG. 1b wherein each light pipe 110 in set 118A is spaced from at least some of the other light pipes 110 in set 118A (with these light pipes 110 also simply being labeled A at their bundled input ends 108); each light pipe 110 in set 118B is similarly spaced from at least some of the other light pipes 110 in set B (with these light pipes 110 also simply being labeled B at their bundled input ends 108); etc. Overall, the desired objective is to have each set 118 of light pipes 110 receive approximately the same light from the light source 102, and since the intensity, wavelength, and/or other qualities of the emitted light may vary about the image of the light source 102 (since it is in effect the projected image of the light source 102 which is received by the input ends 108 of the light pipes 110), it is useful to have all sets 118 of light pipes 110 have an approximately equal distribution about the area of the light receiving bundle 116. FIG. 1b shows such an arrangement, wherein each of the sets 118A, 118B, 118C, and 118D has at least substantially the same spatial distribution of light pipes 110 as any others of the sets 118 about the area of the input bundle 116. Additionally, the input ends 108 are preferably maintained in the bundle 116 so that they are collectively surrounded by a circumferential boundary 120 which is shaped at least substantially complementary to the output light image 106 from the light source 102. For example, in FIG. 1a, the projected light image from the filament 104 in the light source 102 is substantially polygonal (more precisely, substantially rectangular), and thus the bundled input ends 108 of the light pipes 110 in FIG. 1b are restrained to rest within a complementary polygonal boundary 120, the boundary 120 being sized and shaped to closely conform to the projected image 106. By shaping the boundary 120 of the bundle 116 to be complementary to the output light image 106, the sets 118 are closely coupled to the light source 102 to transmit optimal (or nearly so) light therefrom. At the same time, the light pipes 110 of each set 118 are such that each set 118 receives approximately the same light from the output light image 106 and transmits it to the output ends 114 of its light pipes 110.

At the output ends 114, the sets 118 provide light to several sample chambers 122 (with a series of some number N of sample chambers 122 being shown in FIG. 1a), with each sample chamber 122 being appropriate for receiving samples to be spectrometrically analyzed. One of the sets 118 also preferably extends to a reference location 124 isolated from the sample chambers 122. The light provided to the sample chambers 122 is in turn received by sample detectors 126 (with N sample detectors 126 being shown in FIG. 1a), and a reference detector 128 is also preferably provided to receive light at the reference location 124 directly from the output ends 114 of one of the sets 118 (i.e., without receiving the light from am intervening sample chamber 122).

By use of the foregoing arrangement, one can spectrometrically examine some number N of samples (see FIG. 1a) while simultaneously obtaining a reference reading, so that the readings from the sample detectors 126 can be compared to a simultaneously obtained "datum" measurement from the reference detector 128 for purposes of calibration/validation. This arrangement can take a number of forms, e.g., that of FIG. 1a, in each sample chamber 122 has its own detector 126 and the reference detector 128 takes measurements simultaneously with those taken from the sample detectors 126. An alternative arrangement is depicted in FIG. 2, wherein there are fewer sample detectors 226 than sample chambers 222, and the sample detector 226 sequentially moves between the chambers 222 to be analyzed, with the reference detector 228 also taking measurements simultaneously with those taken from the sample detector 226. As an alternative arrangement the readings from the sample detectors can be compared to measurements which are not simultaneously captured from the reference detector. As an example, in the arrangement of FIG. 3, the sample detectors 326 are used to simultaneously collect readings from all of the sample chambers 322, and then the sample detectors 326 are moved in sequence to the reference location 324 so that reference measurements may be captured from each. Thus, each detector 326 captures both sample and reference measurements in sequence.

Further advantages, features, and objects of the invention will be apparent from the following detailed description of the invention in conjunction with the associated drawings.

DETAILED DESCRIPTION OF PREFERRED VERSIONS OF THE INVENTION

Figure 1A:
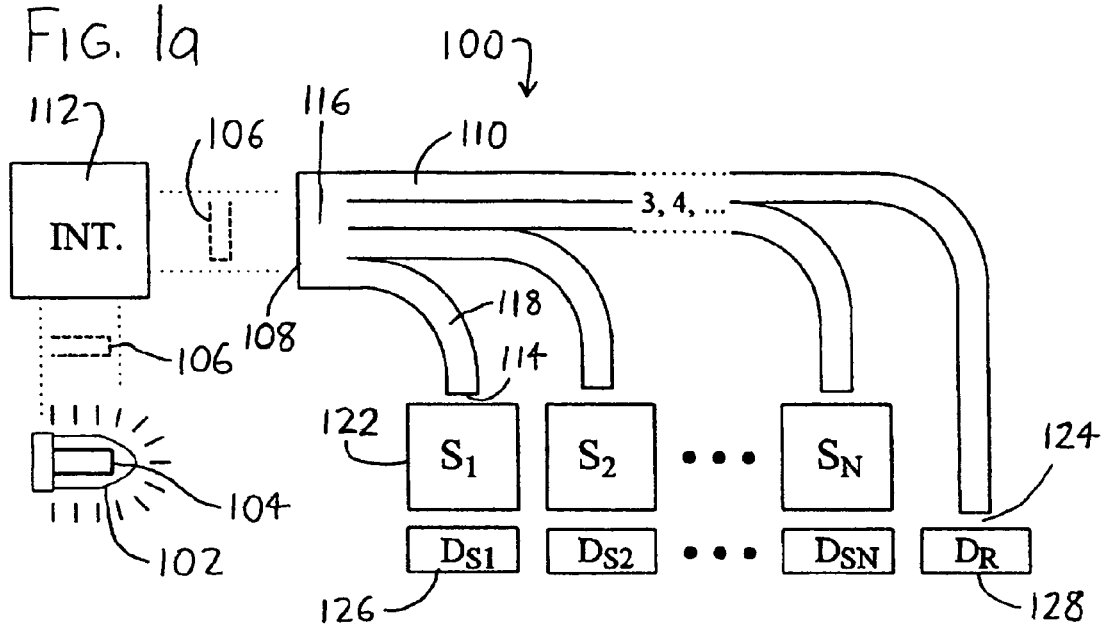
FIG. 1a is a simplified schematic view of a spectrometer 100 exemplifying the concepts of the invention, wherein the image 106 of a light source 102 is projected onto a bundle 116 of light pipes 110, with the light pipes 110 then branching into N 1 sets 118 to illuminate N sample detectors 126 (via N sample chambers 122) and a reference detector 128.
Figure 1B:
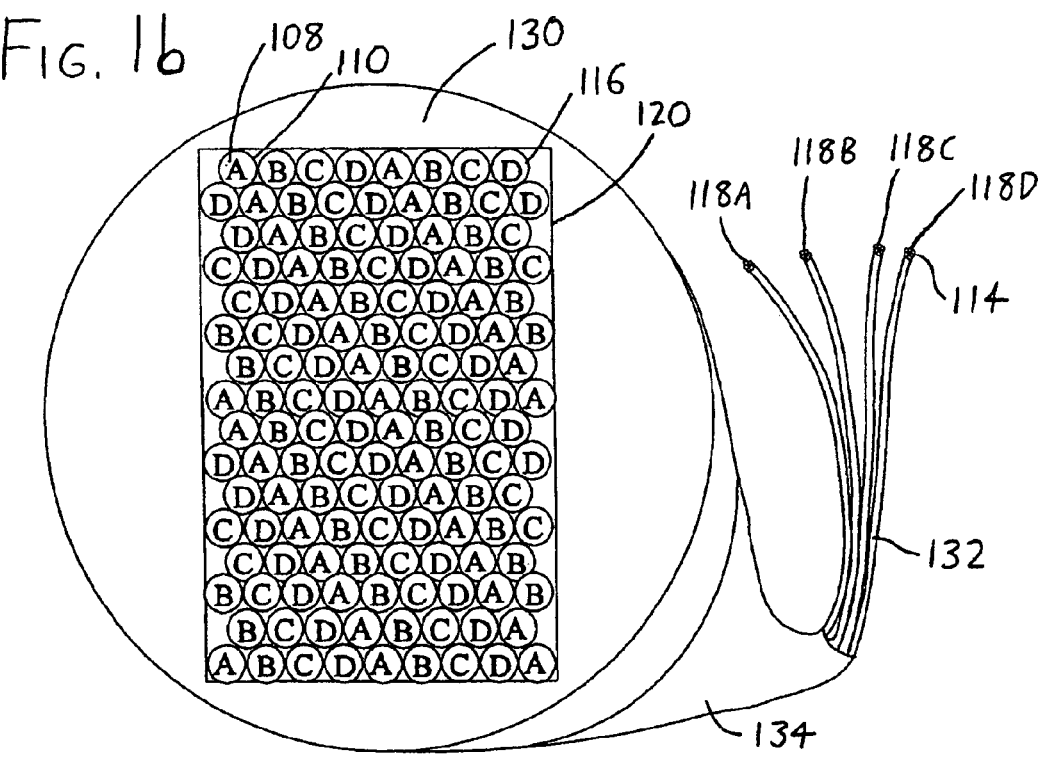
FIG. 1b is a more detailed perspective view of the light pipes 110 of FIG. 1, wherein the bundled input ends 108 of the light pipes 110 are shown in the foreground, and with the lengths of the light pipes 110 descending into the background before branching into sets 118A, 118B, 188C, and 118D and terminating at their output ends 114.

To expand on the discussion given in the foregoing Summary of the Invention of this document, referring to FIG. 1b, the light pipes 110 preferably take the form of identical fiberoptic cables which extend from their bundled input ends 108 to divide into sets 118, with the same number of light pipes 110 per set 118, and with each set 118 having at least substantially the same amount of input area per unit area across the input bundle 116. In FIG. 1b, this is provided by situating the input ends 108 of the light pipes 110 from each set 118 in a regular array, i.e., in a predictable A, B, C, D arrangement. However, it should be understood that the light pipes from each set 118 could be essentially randomly arrayed at the input bundle 116 so long as each set 118 receives approximately the same light per unit area across the input bundle 116.

FIG. 1b also depicts a preferred bundling arrangement, wherein the input ends 108 of the light pipes 110 are constrained to fit within a boundary 120 which is complimentary to the output light image 106 from the interferometer 112 by fitting the input ends 108 within a windowed cap 130 (the window being defined by the boundary 120). The light pipes 110 are thus held in a fixed array throughout the length of the cap 130 (i.e., descending into FIG. 1b), after which light pipes 110 spaced across the input bundle 116 may be collected into the sets 118A, 118B, 118C, and 118D. The light pipes 110 within these sets 118A, 118B, 118C, and 118D are shown bound within protective covering sheaths 132 in FIG. 1b (and with each of the sets 118 further being shown bound within an overall bundle sheath 134 extending from the cap 130).

It should be understood that the four sets 118 depicted in FIG. 1b are only exemplary, and fewer or greater numbers of sets may be included depending on how many sample chambers 122, sample detectors 126, and reference detectors 128 are to be supplied with light. Similarly, the number of light pipes within each set 118 may vary, as well as the manner in which they are arrayed at the input bundle 116 (as noted previously). In some cases, it may be desirable to have different sets 118 receive different types or amounts of light at their input ends 108. To illustrate, it might be desirable to have different ones of the sample chambers 122 receive light of different intensities where different chambers 122 are to receive different components of a multiphase mixture, e.g., one chamber 122 receiving a denser or solid (and thus usually more opaque) fraction, another chamber 122 receiving a more translucent liquid fraction, another chamber 122 receiving a highly transparent gas fraction, etc. In this case, selected sets 118 might include more light pipes 110, or light pipes 110 having greater diameter, so that this set(s) 118 might transmit more light than other sets 118 (which can be useful for obtaining more accurate measurements from more opaque samples). Additionally or alternatively, it might be desirable to have certain sets 118 (and thus their sample chambers 122) receive different wavelength ranges appropriate for different types of samples. In this case, different sets 118 might be formed of light pipes 110 which selectively pass desired wavelength ranges and block others.

Figure 2:
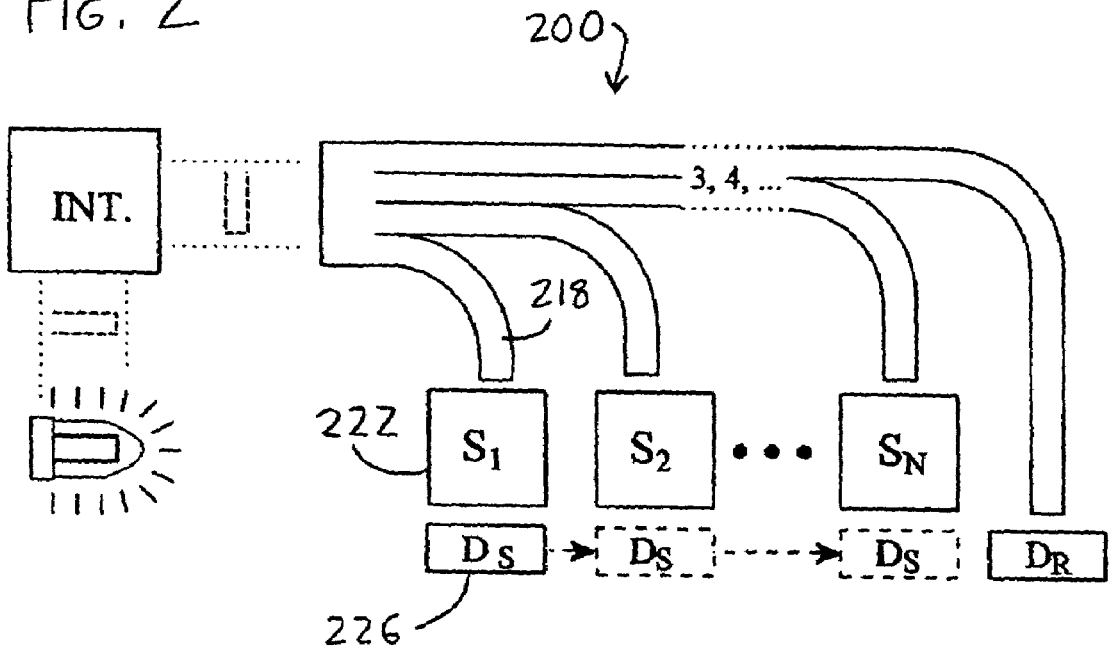
FIG. 2 is a simplified schematic view of a spectrometer 200 presenting an alternative to that of FIG. 1a, wherein a single sample detector 226 is provided, and wherein this sample detector 226 moves between different light pipe sets 218 and sample chambers 222 (as depicted in phantom/dashed lines) to take measurements therefrom while the reference detector 228 simultaneously takes reference readings directly from one of the sets 218.
Figure 3:
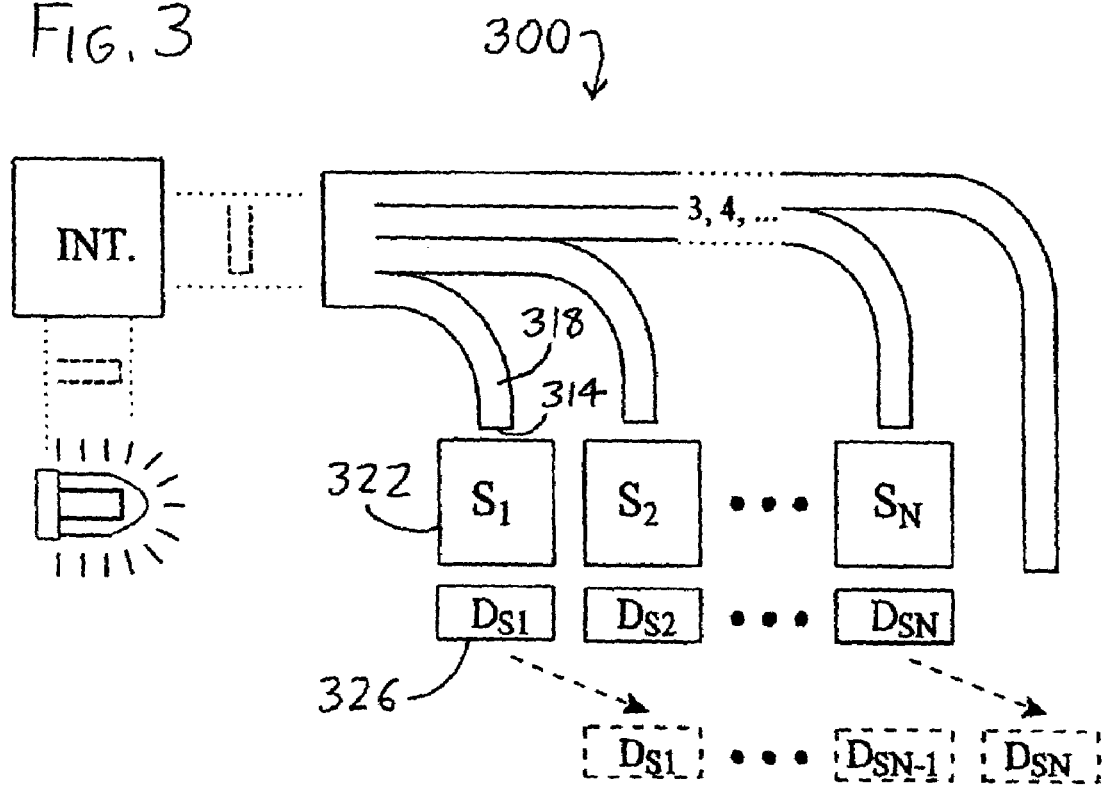
FIG. 3 is another simplified schematic view of a spectrometer 300 presenting an alternative to that of FIGS. 1a and 2, wherein each sample chamber 322 is provided with a sample detector 326, and after these detectors 326 take measurements from their corresponding sample chambers 322, each is sequentially moved to the reference location 324 (the start of this step being depicted in phantom/dashed lines in FIG. 3) to obtain reference measurements.

Further, it should be understood that the arrangements of FIGS. 1A, 2, and 3 are merely exemplary, and many possible arrangements exist beyond those depicted. For example, each of the sample chambers 222 in FIG. 2 could be replaced with a row or other set of sample chambers (descending into the view of FIG. 2, i.e., with other chambers 222 being behind those shown), and the detectors 226 and 228 could likewise be replaced with a row or other set of detectors 226 and 228. During analysis, the row of sample detectors 226 could then move from row to row of sample chambers 222 while the row of reference detectors 228 would take reference measurements simultaneously. Such an arrangement would effectively resemble a combination of arrangements of FIG. 1b and FIG. 2, wherein a two dimensional array of chambers 222 and detectors 226/228 is provided, and wherein FIGS. 1B and 2 each depict one dimension of this array. Such an arrangement might also only use one reference detector 228 rather than several, though multiple detectors 228 (e.g., having different sensitivities over different wavelength ranges) may be more useful where qualitatively (and/or quantitatively) different light is passed by different sets 218.

Similarly, the arrangement of FIG. 3 might be combined with the arrangement of FIG. 1b, wherein the FIG. 3 arrangement has each of its sample chambers 322 and detectors 326 replaced with rows of chambers 322 and detectors 326, with each chamber 322 being illuminated by its own light pipe set 318. In this case, the light pipe set 318 illuminating the reference location 324 in FIG. 3 might also be replaced by multiple light pipe sets 318 illuminating multiple reference locations 324, each of which later receives corresponding detectors 226 in sequence.

Additionally, in the arrangements of FIGS. 2 and 3, it should be understood that it is not necessary that the detectors 226/326 move relative to fixed light pipe sets 218/318, and it is possible that the light pipe sets 218/318 (and chambers 222/322) might move with respect to the detectors 226/326. For example, in the arrangement of FIG. 3, the light pipe set 318 illustrated as illuminating the reference location 324 might have its output ends 314 moved to illuminate each of the sample detectors 326 in turn (assuming no interference from the sample chambers 322 or other components).

The light source 102 need not take the form of an incandescent filament 104, and could instead take the form of a light emitting diode, laser, or other source of light (whether multichromatic or monochromatic), with different types of light sources being more suitable for different types of spectrometry applications. Since the projected image 106 of the light source 102 may vary in accordance with the type of light source 102 being used, it should be understood that the shape and size of the boundary 120 of the light pipe bundle 116 may vary with the light source 102 used so that the light pipes 110 may complementarily receive the light source image 106 at their input ends 108.

The light pipes 110 preferably (but need not) take the form of fiberoptic cables, and they could instead take the form of other light transmitting media, e.g., gel tubes, hollow tubes with internally reflecting surfaces, translucent films or other translucent members, or other matter which directs light along the desired path (preferably with high internal reflection such that minimal light loss occurs). Fiberoptic cables, being readily available and relatively inexpensive, are merely the presently preferred form of the light pipes 110. Further, the light pipes 110 need not be continuous between their input and output ends 108 and 114 and may include different media along their lengths, e.g., a portion of a length of a light pipe 110 could transmit light into an air gap for receipt into the remaining length of the light pipe 110.

The sample chambers 122 may also be provided in a variety of forms, e.g., fully or partially enclosed cells, wells, or other volumes, flow through channels, etc. The invention may be implemented with either static samples or those that are time resolved, e.g., samples whose composition changes over time owing to chemical reactions or other events. Additionally, it should be understood that while simultaneous or sequential analysis of multiple samples is discussed above, this can take the form of simultaneous or sequential analysis of multiple regions on the same sample. In this case, the sample might be divided into separate sample chambers, or it might remain as a unitary volume of material in a single chamber, wherein the single chamber is subdivided into a number of effective smaller chambers (e.g., the chamber receives light from the output ends 114 of several light pipes 110 spaced about the chamber, preferably in such a manner that there is no crosstalk between the light pipes 110 and their detectors 126). In this case, the multiregion analysis of the unitary sample is effectively equivalent to the analysis of several samples.

The detectors 126/128 may be any photosensitive element suitable for use as a detector, with a variety of germanium (Ge), silicon (Si), indium gallium arsenide (InGaAs), and other detectors being readily available from suppliers. It should be understood that the detectors 126 need not receive light directly from sample chambers 122, and instead the light from the sample chambers 122 may be transmitted to detectors 126 via further light pipes or other means of light transmission. Such an arrangement can be useful since all detectors 126 might then be more conveniently located in a climate controlled location so that they experience the same temperatures and other ambient conditions, thereby reducing their relative drift.

The invention may be implemented in any suitable molecular spectrometer, including infrared (IR), near infrared (NIR), ultraviolet (UV Vis), Raman, and other spectrometers using Fourier Transform (FT) or other analysis techniques. Exemplary spectrometers which might implement the invention include the NICOLET and ANTARIS FT IR and FT NIR spectrometers provided by Thermo Electron LLC (Madison, Wis., USA).

Since the foregoing discussion is intended to merely present preferred versions of the invention, it should be understood that the invention is not intended to be limited to these preferred versions, but rather is intended to be limited only by the claims set out below. Thus, the invention encompasses all different versions that fall literally or equivalently within the scope of these claims.

What is claimed is:

1. A spectrometer comprising:
   a. a light source having a filament therein;
   b. at least two sample chambers;
   c. multiple light pipes having input ends adjacently arrayed in a bundle and opposing output ends, wherein:
      (1) the bundled input ends receive light from the light source, the light including an image of the filament,
      (2) the bundle has a profile, as seen on a plane oriented at least substantially perpendicular to an axis along which the image of the filament travels to the input ends, shaped at least substantially complementary to the image of the filament, and
      (3) the light pipes define independent optical paths providing light from the light source to each of:
         (a) the sample chambers, and
         (b) a reference location isolated from the sample chambers,
         wherein none of the paths receives light from any of the other optical paths;
   d. at least two detectors wherein:
      (1) at least one of the detectors is a reference detector receiving light from the reference location, and
      (2) at least one of the detectors is a chamber detector receiving light from the light source via one of the sample chambers,
      whereby measurements generated by the reference and chamber detectors may be compared.

2. The spectrometer of claim 1 wherein at least some of the optical paths each include two or more light pipes having input ends nonadjacently spaced about the bundle.

3. The spectrometer of claim 1 wherein:
   a. each of the optical paths to the sample chambers and the reference location includes multiple light pipes, and
   b. at least some of the light pipes within each of the optical paths have input ends which are nonadjacently spaced within the bundle by the input ends of light pipes of other optical paths.

4. The spectrometer of claim 3 wherein the bundled input ends of the light pipes are collectively surrounded by an at least substantially noncircular circumferential boundary.

5. The spectrometer of claim 3 wherein the bundled input ends of the light pipes are collectively surrounded by an at least substantially polygonal circumferential boundary.

6. The spectrometer of claim 1 wherein at least some of the optical paths to the sample chambers and reference location differ in at least one of:
   a. the numbers of light pipes included therein;
   b. the diameters of the light pipes included therein; and
   c. the wavelengths of Light passed by the light pipes included therein.

7. The spectrometer of claim 6 wherein at least some of the optical paths include two or more light pipes with input ends which are nonadjacently spaced within the bundle by light pipes of other ones of the optical paths.

8. The spectrometer of claim 1 wherein:
   a. at least some of the optical paths are each provided by multiple light pipes, and
   b. the boundary circumferentially surrounding the bundled input ends is at least substantially noncircular.

9. The spectrometer of claim 8 wherein the boundary circumferentially surrounding the bundled input ends is at least substantially polygonal.

10. The spectrometer of claim 1 further comprising an interferometer interposed between the light source and the bundled input ends of the light pipes, wherein the interferometer provides light from the light source to the bundled input ends.

11. The spectrometer of claim 1 wherein:
    a. at least one of the detectors receives light from the light source via one of the sample chambers, and
    b. at least one of the detectors simultaneously receives light from the reference location.

12. The spectrometer of claim 1 wherein at least one of the detectors is movable between sample chambers, whereby the detector receives light from the light source via different sample chambers in sequence.

13. The spectrometer of claim 1 wherein one or more of the detectors receives light from the reference location after receiving light via one of the sample chambers.

14. The spectrometer of claim 1 wherein at least one of the detectors is movable between one of the sample chambers and the reference location.

15. The spectrometer of claim 1 wherein at least one of:
    a. the light pipes providing the light from the light source to the reference location, and
    b. the one or more detectors receiving the light from the reference location, is movable relative to the other.

16. A spectrometric method comprising the steps of:
    a. providing light along several light pipes from a light source to several sample chambers, the sample chambers bearing samples to be spectrometrically analyzed, with the light then being received by chamber detectors from the sample chambers, and wherein:
       (1) the light pipes include input ends which receive the light from the light source, with the input ends being bundled;
       (2) at least some of the sample chambers each receive light from the light source via several of the light pipes; and
       (3) at least some of these several light pipes have input ends spaced from each other within the bundle by light pipes providing light to other ones of the sample chambers;
    b. providing light along several light pipes from the light source to a reference detector, with the reference detector being isolated from receiving light from the sample chambers, wherein at least some of the several light pipes providing light from the light source to the reference detector have input ends spaced from each other by light pipes which provide light from the light source to the sample chambers;
    c. comparing chamber light measurements generated by the chamber detectors to a reference light measurement generated by the reference detector.

17. The spectrometric method of claim 16 wherein at least some of the sample chambers differ in at least one of:
    a. the numbers of light pipes from which the sample chambers receive light;
    b. the diameters of the light pipes from which the sample chambers receive light; and c. the wavelengths of light passed by the light pipes from which the sample chambers receive light.

18. The spectrometric method of claim 16 wherein the steps of:
   a. providing light to the sample chambers, and
   b. providing light to the reference detector, occurs simultaneously.

19. The spectrometric method of claim 16 wherein the step of providing light to the sample chambers is performed by providing light to different ones of the sample chambers in sequence.

20. The spectrometric method of claim 19 wherein light is provided to the reference detector simultaneously with light being provided to each of the sample chambers.

21. A spectrometric method comprising the steps of:
   a. providing light alone several light pipes from a light source to several sample chambers, the sample chambers bearing samples to be spectrometrically analyzed, with the light then being received by chamber detectors from the sample chambers, and wherein:
      (1) the light pipes include input ends which receive the light from the light source, with the input ends being bundled;
      (2) at least some of the sample chambers each receive light from the light source via several of the light pipes; and
      (3) at least some of these several light pipes have input ends spaced from each other within the bundle by light pipes providing light to other ones of the sample chambers;
   b. providing light alone several light pipes from the light source to a reference detector, with the reference detector being isolated from receiving light from the sample chambers; and
   c. comparing chamber light measurements generated by the chamber detectors to a reference light measurement generated by the reference detector,
   wherein the step of providing light to the reference detector occurs at a different time than the step of providing light to the sample chambers.

22. The spectrometric method of claim 16 wherein:
   a. the light source has a filament therein, and emits an image of the filament to the bundled input ends; and
   b. the bundle has a profile, as seen on a plane oriented at least substantially perpendicular to an axis along which the image of the filament travels to the input ends, shaped at least substantially complementary to the image of the filament.

23. A spectrometer comprising:
   a. a light source;
   b. at least two sample chambers;
   c. Multiple light pipes having input ends adjacently arrayed in a bundle and opposing output ends, wherein:
      (1) the bundled input ends receive light from the light source, and
      (2) the light pipes define independent optical paths providing light from the light source to each of:
         (a) the sample chambers, and
         (b) a reference location isolated from the sample chambers,
      wherein none of the paths receives light from any of the other optical paths;
   d. at least two detectors wherein;
      (1) at least one of the detectors is a reference detector receiving light from the reference location, and
      (2) at least one of the detectors is:
         (a) a chamber detector receiving light from the light source via one of the sample chambers,
         (b) movable between sample chambers, whereby the detector receives light from the light source via different sample chambers in sequence,
      whereby measurements generated by the reference and chamber detectors may be compared.

24. A spectrometer comprising:
a. a light source;
b. at least two sample chambers;
c. multiple light pipes having input ends adjacently analyzed in a bundle and opposing output ends, wherein:
   (1) the bundled input ends receive light from the light source, and
   (2) the light pipes define independent optical paths providing light from the light source to each of:
      (a) the sample chambers, and
      (b) a reference location isolated from the sample chambers,
   wherein none of the paths receives light from any of the other optical paths;
d. at least two detectors wherein;
   (1) at least one of the detectors is a reference detector receiving light from the reference location, and
   (2) at least one of the detectors is a chamber detector receiving light from the light source via one of the sample chambers,
   and wherein one or more of the detectors receives light from the reference location after receiving light via one of the sample chambers,
   whereby measurements generated by the reference and chamber detectors may be compared.

25. A spectrometer comprising:
a. a light source;
b. at least two sample chambers;
c. multiple light pipes having input ends adjacently arrayed in a bundle and opposing output ends, wherein:
   (1) the bundled input ends receive light from the light source, and
   (2) the light pipes define independent optical paths providing light from the light source to each of:
      (a) the sample chambers, and
      (b) a reference location isolated from the sample chambers,
   wherein none of the paths receives light from any of the other optical paths;
d. at least two detectors wherein:
   (1) at least one of the detectors is a reference detector receiving light from the reference location,
   (2) at least one of the detectors is a chamber detector receiving light from the light source via one of the sample chambers, and
   (3) at least one of the detectors is movable between one of the sample chambers and the reference location,
   whereby measurements generated by the reference and chamber detectors may be compared.

26. A spectrometer comprising:
a. a light source;
b. at least two sample chambers;
c. multiple light pipes having input ends adjacently arrayed in a bundle and opposing output ends, wherein:
   (1) the bundled input ends receive light from the light source, and
   (2) the light pipes define independent optical paths providing light from the light source to each of:
      (a) the sample chambers, and (b) a reference location isolated from the sample chambers, wherein none of the paths receives light from any of the other optical paths;

d. at least two detectors wherein:

(1) at least one of the detectors is a reference detector receiving light from the reference location, with at least one of the reference detector and the light pipes providing the light from the light source to the reference location being movable relative to the other, and (2) at least one of the detectors is a chamber detector receiving light from the light source via one of the sample chambers, whereby measurements generated by the reference and chamber detectors may be compared.

* * * * *

UNITED STATES PATENT AND TRADEMARK OFFICE
CERTIFICATE OF CORRECTION

PATENT NO. : 7,339,668 B2  
APPLICATION NO. : 11/253853  
DATED : March 4, 2008  
INVENTOR(S) : Ebersole et al.

Page 1 of 1

It is certified that error appears in the above-identified patent and that said Letters Patent is hereby corrected as shown below:

Claim 21, line 2  
replace "a. providing light alone"  
with --a. providing light along--

Claim 21, line 17  
replace "b. providing light alone"  
with --b. providing light along--

Claim 24, lines 4-5  
replace "adjacently analyzed"  
with --adjacently arrayed--

Signed and Sealed this

Eleventh Day of November, 2008

JON W. DUDAS  
*Director of the United States Patent and Trademark Office*

UNITED STATES PATENT AND TRADEMARK OFFICE
CERTIFICATE OF CORRECTION

PATENT NO. : 7,339,668 B2 Page 1 of 1
APPLICATION NO. : 11/253853
DATED : March 4, 2008
INVENTOR(S) : Ebersole et al.

It is certified that error appears in the above-identified patent and that said Letters Patent is hereby corrected as shown below:

Column 9, Claim 21, line 16
replace "a. providing light alone"
with --a. providing light along--

Column 9, Claim 21, line 31
replace "b. providing light alone"
with --b. providing light along--

Column 10, Claim 24, lines 11-12
replace "adjacently analyzed"
with --adjacently arrayed--

This certificate supersedes the Certificate of Correction issued November 11, 2008.

Signed and Sealed this

Ninth Day of December, 2008

JON W. DUDAS
*Director of the United States Patent and Trademark Office*